United States Patent [19]

Riva

[11] 4,402,601
[45] Sep. 6, 1983

[54] FUNDUS CAMERA-BASED RETINAL LASER DOPPLER VELOCIMETER

[76] Inventor: Charles E. Riva, 978 Conestoga Rd., Berwyn, Pa. 19312

[21] Appl. No.: 221,614

[22] Filed: Dec. 31, 1980

[51] Int. Cl.³ ............................ G01P 3/36; A61B 3/14
[52] U.S. Cl. .................................. 356/28.5; 128/666; 351/206; 351/221
[58] Field of Search ............... 128/666, 691; 356/28.5; 351/7, 16

[56] References Cited

U.S. PATENT DOCUMENTS

| | | | |
|---|---|---|---|
| 3,770,342 | 11/1973 | Dudragne | 351/7 |
| 3,780,979 | 12/1973 | Guillebon | 351/16 |
| 3,941,477 | 3/1976 | Schodl | 356/28 |
| 3,954,329 | 5/1976 | Pomerantzeff | 351/16 |
| 4,102,563 | 7/1978 | Matsumura et al. | 351/7 |
| 4,102,565 | 7/1978 | Takizawa | 351/14 |
| 4,109,647 | 8/1978 | Stern et al. | 356/28.5 |
| 4,142,796 | 3/1979 | Riva | 356/28.5 |
| 4,166,695 | 9/1979 | Hill et al. | 356/28.5 |
| 4,206,999 | 6/1980 | Keller | 356/28.5 |

OTHER PUBLICATIONS

C. E. Riva et al., Applied Optics, Jul. 1, 1979, vol. 18, No. 13, p. 2301.

*Primary Examiner*—S. C. Buczinski
*Attorney, Agent, or Firm*—Robert C. Podwil

[57] ABSTRACT

A bidirectional laser Doppler velocimeter provides absolute measurement of the speed of red blood cells flowing in individual retinal vessels. A standard retinal camera is used, and the need for a contact lens for the subject eye is eliminated. The laser beam is delivered to the eye through the fundus illumination optical system of the camera. Target fixation is done with the eye under examination. The measurements are independent from the ocular refraction; only the axial length of the eye need be determined. The instrument markedly simplifies the technique of retinal blood flow measurement.

15 Claims, 10 Drawing Figures

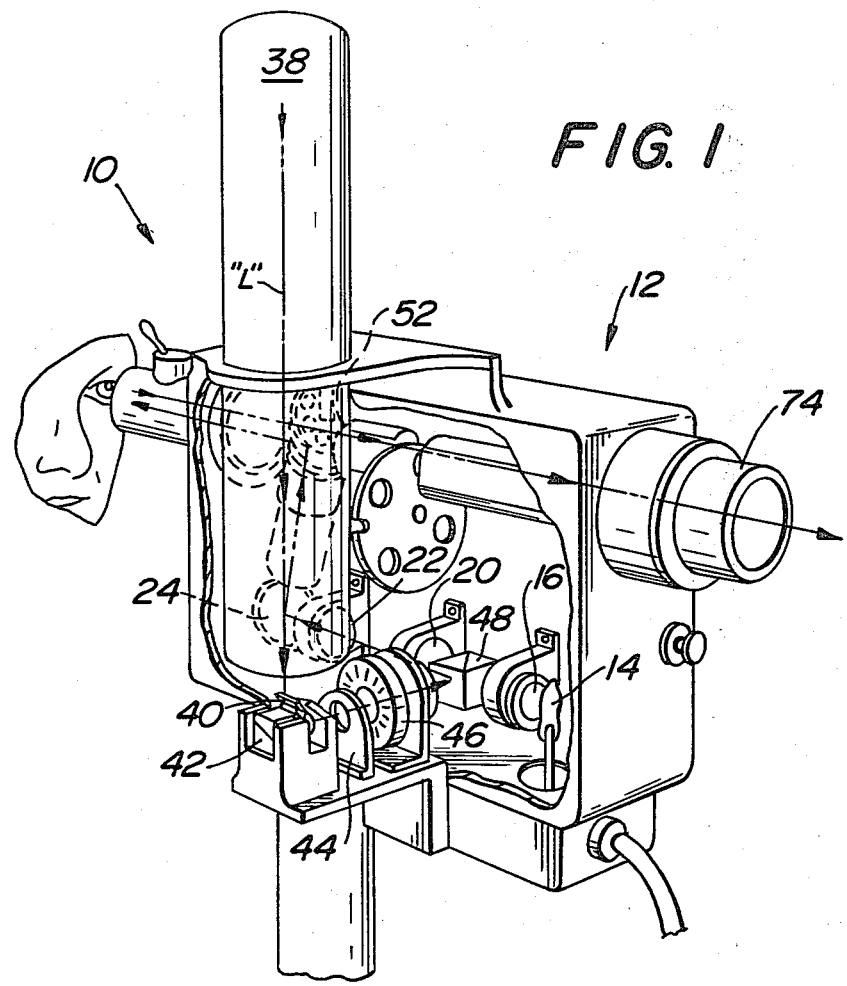
FIG. 1
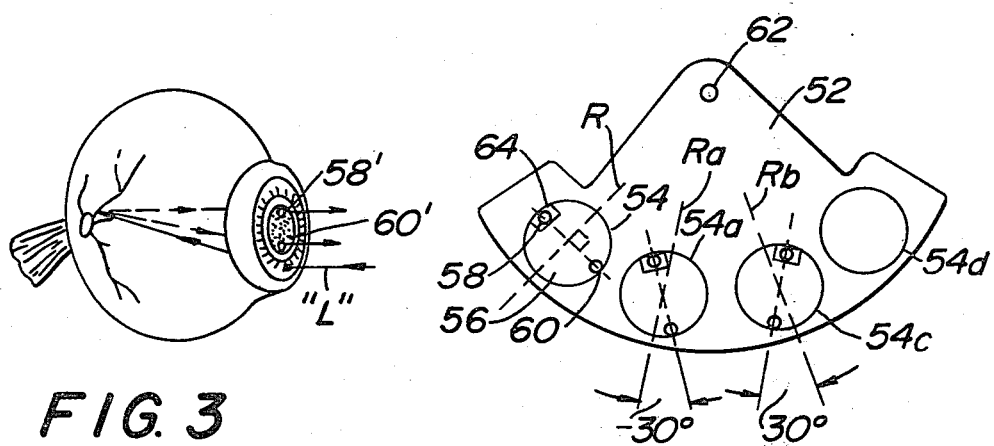
FIG. 3
FIG. 4

OSCILLOSCOPE DISPLAY

FUNDUS CAMERA-BASED RETINAL LASER DOPPLER VELOCIMETER

BACKGROUND OF THE INVENTION

This invention relates in general to apparatus for detecting the velocity of blood flowing in a vessel of the eye, and more particularly, to a fundus camera-based retinal laser Doppler velocimeter. The apparatus provides for absolute measurement of the speed of red blood cells flowing in individual retinal vessels, and can be routinely used by medically trained persons, without the need for placement of a contact lens on the patient's eye or resort to invasive techniques.

As was pointed out in U.S. Pat. No. 4,142,796, issued Mar. 6, 1979, to Charles E. Riva, and elsewhere, the ability to measure the velocity of blood flowing in a single blood vessel or in a capillary bed is very useful for medical purposes. Impairment of the blood flow in the tissues of the ocular fundus, or the retina of the eye, is associated with a large number of diseases that can lead to grave visual disorders. Blood flow measurements have also been used to differentiate between living and nonliving tissues, to determine which tissues require surgical removal and which should not be removed.

The feasibility of using laser doppler velocimetry (hereafter referred to as "LDV") to measure blood flow in individual retinal vessels was demonstrated in 1972 by Riva et al (C. E. Riva, B. Ross and G. B. Benedek, Investigative Ophthalmology, Vol. 11, pps. 936 et seq., Nov., 1972), who measured the Doppler-shift frequency spectrum of laser light scattered from red blood cells flowing in a retinal artery of an anesthetized rabbit. The maximum Doppler frequency shift $f_{max}$ arising from the light scattered by the red blood cells flowing at the maximum speed $V_{max}$ was estimated from the spectrum. $V_{max}$ was calculated from $f_{max}$ and from estimates of the intraocular scattering geometry using the general relation:

$$V_{max} = \frac{\lambda f_{max}}{n(\cos\theta_s - \cos\theta_i)}, \quad (1)$$

where $\lambda$ is the wavelength in vacuo of the incident laser light, n is the refractive index of the flowing medium, $\theta_i$, is the intraocular angle between the incident beam and the flow direction, and $\theta_s$ is the intraocular angle between the collected scattered light and the flow direction. It was assumed that the incident laser beam was perpendicular to the flow direction.

It has been shown (G. T. Feke and C. E. Riva, J. Opt. Soc. Am. Vol. 68, pps. 526 et seq., 1978) that $f_{max}$ can be determined from Doppler-shift frequency spectra obtained from human retinal vessels using short measurement times (less than one second), and further, it has been shown that $V_{max}$ can be determined by a procedure involving the collecting of light scattered by red blood cells in two distinct directions separated by a known angle (C. E. Riva, G. T. Feke, B. Eberli and V. Benary, Applied Optics, Vol. 18, pps. 2301 et seq July 1, 1979). Analysis of the collected light, it has been found, yields an absolute measure of $V_{max}$ that is independent of the exact orientation of the vessel and of the relative angular orientation of the incident and scattered light beams with respect to the flow direction. In the present apparatus, bidirectional LDV is performed using apparatus, the basic component of which is a standard retinal camera. The need for a contact lens is eliminated, and the laser beam is delivered to the eye through the fundus illumination optical system of the camera. Use of the present apparatus markedly simplifies the technique of retinal blood flow measurement.

Thus, bidirectional laser Doppler velocimetry allows absolute measurements of the speed of red blood cells in retinal vessels. In this technique, Doppler shift frequency spectra (hereafter referred to as "DSFS") of laser light scattered from the red blood cells are recorded for two directions of the scattered light, while the direction of the incident beam remains constant. These DSFS, when obtained in short measurement times, exhibit large fluctuations in spectral power up to a cutoff at a frequency $f_{max}$ that arises from light scattered by red blood cells flowing at the maximum speed, $V_{max}$, at the center of the vessel. $\Delta f = f_{2\,max} - f_{1\,max}$ is the difference between the cutoff frequencies obtained from DSFS recorded in two directions, $K_1$ and $K_2$. $V_{max}$ is obtained from these DSFS using the relation:

$$V_{max} = \frac{\lambda \Delta f}{n \Delta \alpha \cos\beta}, \quad (2)$$

$\lambda$ is the wavelength of the incident laser beam, n, the index of refraction of the flowing medium, $\alpha$, the angle between $\vec{K}_1$ and $\vec{K}_2$ and $\beta$ is the angle between the vector $\vec{V}_{max}$ and its projection on the plane defined by the vectors $\vec{K}_1$ and $\vec{K}_2$.

The first absolute measurements of $V_{max}$ were obtained using a standard slitlamp microscope in conjunction with a low-vacuum corneal contact lens. Use of a contact lens simplifies considerably the determination of the scattering geometry because the lens eliminates the corneal refraction of the Doppler shifted light. Several problems arise, however, when the technique is applied to human subjects: (a) there is a risk of corneal abrasion or infection; (b) there is poor stabilization of the target retina to motion because the fellow (non-target) eye is used for target fixation; (c) changes in intraocular pressure caused by application of the contact lens may affect retinal blood flow; and (d) the slitlamp instrument in its present stage of development does not allow DSFS to be simultaneously recorded for two directions of the scattered light or the determination of $V_{max}$ in vertical vessels.

U.S. Pat. No. 4,166,695, issued Sept. 4, 1979, to Hill et.al. discloses use of a retinal (fundus) camera in the measurement of retinal blood flow, but the Hill et. al. apparatus does not provide absolute measurements of the speed of red blood cells in retinal vessels.

This invention relates, therefore, to a new bidirectional laser Doppler instrument that uses a fundus camera instead of a slitlamp, thus avoiding the need for a contact lens, but still allowing straightforward determination of the scattering geometry, the scattered light being detected in two directions. Moreover, as will be seen, the instrument allows $V_{max}$ to be determined for blood vessels extending in any direction, and provides target fixation for the eye under examination.

SUMMARY OF THE INVENTON

It is a principal object of this invention to provide a means for obtaining an absolute measurement of blood velocity in retinal blood vessels, without the need for use of a contact lens.

Another important object of the invention is to provide an apparatus for absolute measurement of blood velocity which can be used routinely and reliably in medical examinations by persons having no more than ordinary training in the use of common medical instruments.

The above and other objects of this invention are realized, in a presently preferred form of the invention, by apparatus which provides a laser for producing a beam of coherent light, and an optical system for impinging the beam on at least one retinal vessel in which blood is flowing. Additionally, radiation reflected from red blood cells flowing in the vessel are detected and collected in two distinct directions of scattering, separated by a known angle, the Doppler shift frequencies of the respective beams providing a means whereby the absolute velocity of blood flowing in the vessel may be derived. In the presently preferred form of the apparatus, the means for producing the requisite pair of beams comprises a pair of apertures disposed in the path of the reflected radiation. The radiation emerging from the apertures provides the two beams, and analysis of those beams yields an absolute measure of the maximum velocity in the vessel that is independent of the exact orientation of the vessel and the relative angular orientation of the incident and scattered light beams with respect to the flow direction.

BRIEF DESCRIPTION OF THE DRAWINGS

FIG. 1 is a perspective view of apparatus in accordance with the invention.

FIG. 3 is a view of a subject eye, showing the impingement of a fundus-illuminating light on the eye and a laser beam on a retinal vessel.

FIG. 4 is a detailed view of a component of the apparatus shown in FIGS. 1 and 2.

DETAILED DESCRIPTION OF PREFERRED EMBODIMENT

Figure 2:
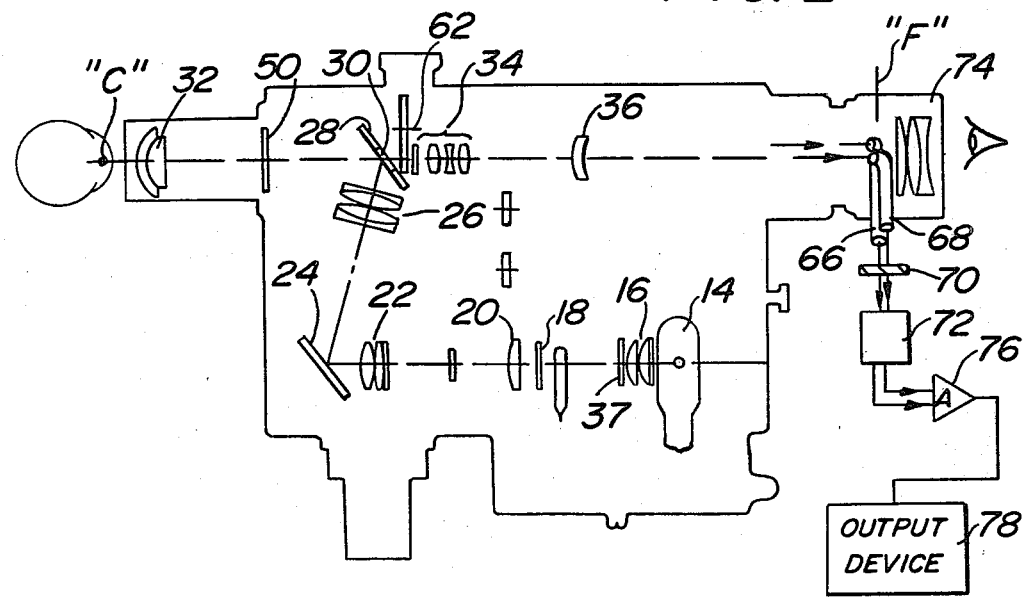
FIG. 2 is a cross-sectional view of apparatus in accordance with the invention, showing certain optical and mechanical details.

Referring now to the drawings in detail, wherein like numerals indicate like elements, there is seen in FIG. 1 a laser Doppler velocimeter designated generally by the reference numeral 10. The basic optical component of the velocimeter 10 is a retinal (or fundus) camera, designated generally by the reference numeral 12. One suitable fundus camera is the Topcon Retinal Camera, model TRC-FE. In general, the camera consists of (1) a fundus illumination system and (2) a system which collects the light reflected from the ocular fundus and focuses it at the retinal image plane "F" in FIG. 2.

Referring now to FIGS. 1 and 2, the fundus illumination system includes a light source in the form of a lamp 14, a condenser lens 16 and an annular aperture 18. The aperture 18 is imaged by lenses 20 and 22, reflection mirror 24, and lens 26 on a reflection mirror 28. The reflection mirror 28 has a central opening 30, the purpose of which is explained below. The light from the lamp 14 is then re-imaged on the cornea "C" of a subject eye, by an objective lens 32.

With regard to the collecting system of the retinal camera 12, the objective lens 32 focuses an aerial image of the subject retina between the objective lens 32 and the reflection mirror 28, and lenses 34 and 36 focus the image at the plane "F".

The opening 30 in the reflection mirror 28 allows only that part of the light reflected from the fundus that passes through the non-illuminated part of the cornea "C" and the opening 30 to reach the image plane "F". The effect of the aperture 18 and the opening 30 in the reflection mirror 28 is to provide an annulus of illumination for the fundus.

Use in the optical train from the lamp 14 of an interference filter 37, which transmits only in the wavelength range of 5500 to 5800 Å, provides red-free illumination of the fundus.

Figure 10:
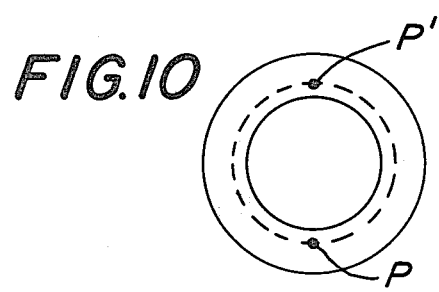
FIG. 10 is a diagrammatic view relating to the manner in which a laser beam may be positioned in using the present apparatus.
Figure 9:
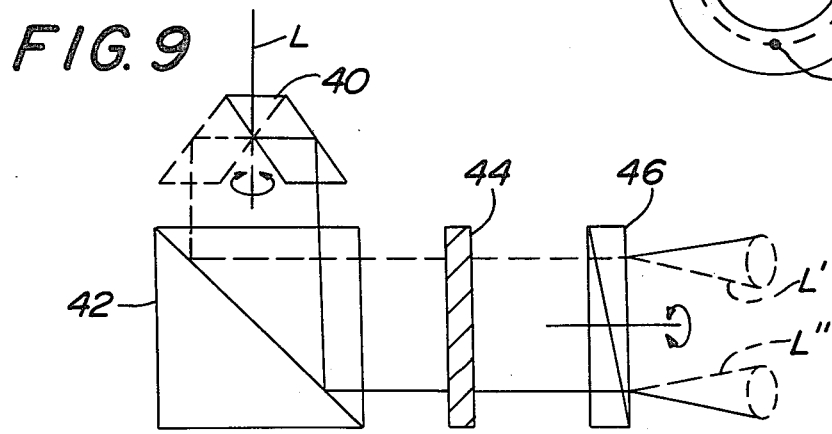
FIG. 9 is a schematic view illustrating aspects of the laser delivery system in apparatus in accordance with the invention.

Referring again to FIG. 1, the retinal camera 12 is provided with a laser delivery system which will now be described. A He-Ne laser beam produced by a laser 38 is delivered to the subject retina along an optical path in part shared with the above-described fundus illumination system. Thus, the laser beam "L" passes through a rhomboid prism 40 that can be rotated for aiming around a vertical axis. The beam L is then deflected horizontally, in the illustrated embodiment, by a beamsplitter 42, is attenuated by a density filter 44, and then passed through a rotary prism 46, the dioptric power of which can be adjusted. The beam L is then deflected into the fundus illumination system by a beamsplitter 48. As is depicted in FIGS. 3, 9 and 10, and described in greater detail below, the above-described system allows the beam L to enter the pupil of the subject eye at any point within the illuminated annulus of the fundus illumination system. Fine positioning of the beam L and its angle of entrance can be varied by adjusting the dioptric power of the rotary prism 46. The above-described laser delivery system provides reflection-free, focal laser illumination of the retina while also allowing fine positioning of the beam. The diameter of the laser beam at the retina, $D_r$, calculated using the relation for a diffraction-limited image, $D_r = 2.1.22\lambda f/D$, is 117 $\mu$m. f is the focal length of Gullstrand schematic eye (22.78 mm) and D is the measured diameter of the beam at the pupil (0.3 mm). The diameter of the laser beam is thus between the diameter of the main retinal arteries and that of the main retinal veins.

For precise target fixation with the eye under examination, a fine cross hair 50 is preferably mounted on the internal fixation system of the retinal camera 12, between the reflection mirror 30 and the objective lens 32.

As has been seen, the collection optics of the retinal camera 12 allows light from the subject retina that passes through the opening 30 on the reflection mirror 28 to be focused at the plane F. The bidirectional means by which reflected and scattered laser light is collected, and the manner in which it may be processed to yield an absolute measurement of blood velocity will now be described.

Referring to FIGS. 1, 2 and 4, there is disposed behind and in close proximity to the reflection mirror 28, a wheel or sector 52 containing a number of openings 54. The openings 54 are covered with a material which is opaque to the laser beam L. One such material suitable for the purposes of this invention is a Kodak green filter No. 57A. Referring to FIG. 4, the filter material 56 is pierced by diametrically spaced apertures 58 and 60. Typically, the apertures 58 and 60 have a diameter of approximately 1.5 millimeters. Because the filter does not transmit at the wavelength of the laser beam L (6328 Å), only laser light passing through the apertures 58 and 60 is transmitted to the plane "F" and the collecting means to be described later.

The wheel or sector 52 is mounted for rotation about a generally horizontal pivot axis 62, so that individual openings 54, 54a, 54b and perhaps others 54d etc. can be placed, if desired, in the optical path. With reference to FIG. 2, the optical path, it will be understood, at this point in the apparatus 10, lies behind the opening 30 in the reflection mirror 28. In other words, selected openings 54, 54a or 54b may be selectively aligned, by rotation of the wheel or sector 52 about the pivot axis 62, with the opening 30.

Referring again to FIG. 4, the apertures 58 and 60 are so disposed that a line between their centers makes an angle of 90 degrees with a radius R of the wheel or sector 52. A line between the centers of the apertures 58, 60 associated with the opening 54a makes an angle of minus 30 degrees with a radius $R_a$ of the wheel or sector 52. A line between the centers of the apertures 58, 60 associated with the opening 54b makes an angle of 30 degrees with a radius $R_b$ of the wheel 52. By offsetting the apertures 58, 60 in the above described manner, it is possible to select an opening 54 in which the orientation of the apertures 58 and 60 correspond generally to the orientation of a retinal vessel under observation. Thus, for example, if it is desired to observe a vessel which extends horizontally, the operator of the apparatus 10 could, by rotation of the wheel or sector 52, select use of the apertures 58, 60 associated with the opening 54. Orientation of the apertures 58, 60 in the direction of blood flow in the vessel maximizes the perceptibility of the Doppler shift. The above-described configuration of the apertures 58, 60 in the various openings 54, 54a and 54b permits selection of one pair of apertures which approximates generally (within ±15 degrees) the direction of any chosen retinal vessel.

Referring now to FIG. 3, the apertures 58 and 60 are imaged by the objective lens 32 into 58' and 60' at the cornea of the subject eye. In other words, the radiation which passes through the apertures 58 and 60 are two beams of reflected and scattered laser radiation which emerge from the cornea at 56' and 58'. In the presently preferred form of the apparatus 10, one of the apertures 58 and 60 of the wheel or sector 52 is provided with a small (2×2 mm), prism 64, conveniently of 1 diopter but possibly of different dioptric power, mounted on its front surface, that is, the surface facing toward the subject eye. The prism 64 displaces the focus of the beam through the aperture 58 by approximately 3 mm at the plane "F". A pair of optical fibers 66 and 68, mounted at the plane "F" on a X-Y micromanipulator (not shown) collect the laser beams. In the presently preferred form of the apparatus, the optical fibers 66 and 68 are of 400 μm diameter. The laser radiation collected by each optical fiber 66, 68 is transmitted through a filter 70, in the preferred embodiment a Kodak red filter No. 29, to a photo-multiplier tube 72 (in the preferred embodiment, RCA 8645), mounted adjacent to the eyepiece 74 of the retinal camera 12. The foregoing radiation-collecting arrangement was described by Riva and Ben-Sira, in Applied Optics, Vol. 14, page 2691 (1975). The output photocurrent is fed through an FET input current-to-voltage amplifier 76, and recorded on magnetic tape by a recorder/producer 78. A Honeywell 5600C FM recorder/producer or equivalent is satisfactory for this purpose. It will be appreciated that being able to detect the Doppler-shifted laser beams in the image plane of the retinal camera 12 has the significant advantage of eliminating unwanted laser radiation scattered from fundus structures adjacent to the site of measurement and from other intraocular structures such as the lens of the eye.

Figure 5:
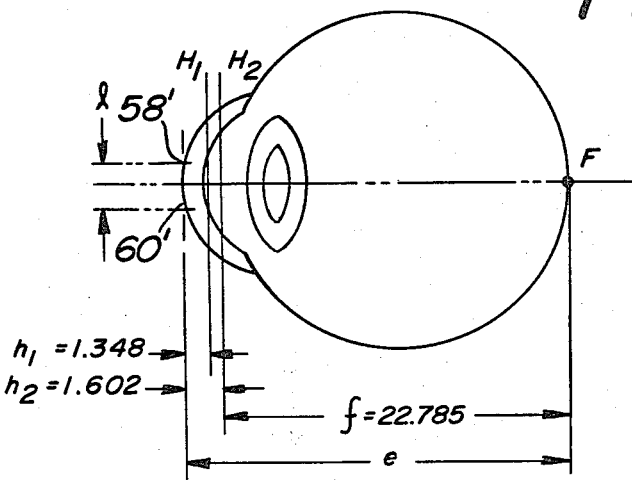
FIG. 5 is a schematic eye, and is illustrative of aspects of measurements made with the present apparatus.

With reference to FIG. 5, the manner in which the intraocular angle α may be determined will now be described.

FIG. 5 shows Gullstrand's schematic eye. $H_1$ and $H_2$ are the first and second principal planes, respectively. The principal planes $H_1$ and $H_2$ are located, respectively, at distances of $h_1$ and $h_2$ from the center of the cornea (see M. Katz, The Human Eye As An Optical System, *Clinical Ophthalmology*, Vol. 1, Chapter 33, T. D. Duane, Editor, Harper & Row Publisher 1979). F in FIG. 5 is the second focal point of the eye, and e the distance from the vertex of the cornea to F. e may also be expressed as the distance between the center of the cornea and the point where the optic axis of the eye intersects the retina. 58' and 60' are virtual images of the apertures 58 and 60.

It will be seen that the virtual apertures 58' and 60' are imaged by the eye at a distance $$b = -\frac{h_1 f}{f - h_1}$$

from $H_2$ and with a magnification of $|f/(f-h_1)|$, where f is the posterior focal length. If l is the distance between the centers of 58' and 60', then α is obtained from the relation:

$$\Delta\alpha = \tan^{-1}\left(\frac{lf}{(f-h_1)(e+b-h_2)}\right) \quad (3)$$

In one operative embodiment of the apparatus 10, the measured magnification between the plane of the apertures 58 and 60 and that of 58' and 60' was 0.242. With such an apparatus, if d is the separation between the centers of the apertures 58 and 60:

$$\Delta\alpha = \tan^{-1}\left(\frac{0.242\, df}{(f-h_1)(e+b-h_2)}\right) \quad (4)$$

From Gullstrand's eye, $f = 22.785$, $h_1 = 1.348$ and $h_2 = 1.602$ mm. Thus $b = 1.433$. Noting that $b - h_2 << e$, and neglecting $h_1$, $$\Delta\alpha \simeq \tan^{-1}\left(\frac{0.257 d}{e}\right) \simeq \frac{0.257 d}{e} \qquad (5)$$

Equation 5 is valid for emmetropic eyes and eyes with axial ametropia (the most common form of ametropia). It shows that the only ocular measurement required to determine $\alpha$ is the axial length of the eye, a measurement that can be done routinely by A-scan ultrasonography with a pecision better than 1%.

Combining Eqs. (5) and (2), $$V_{max} = \frac{3.89\lambda e\, \Delta f}{nd\, \cos\beta} \qquad (6)$$

When the site of measurement at the retina is off center, $\Delta\alpha$ differs from the value calculated above by an amount approximately equal to $1^3/4R^2(x+R)$, where R is the radius of the retina ($=11$ mm) and x is the abscissa of the measurement site, the origin of the coordinate system being at the center of curvature of the retina. Most often $V_{max}$ is obtained from vessels close to the optic nerve, in which case, x is approximately equal to 0.86R, and the difference between $\Delta\alpha$ given by Eq. 5 and the actual angle between the scattered rays $\overline{K_1}$ and $\overline{K_2}$ is only about 0.06°.

When the cutoff frequencies $f_{1\,max}$ and $f_{2\,max}$ are obtained by spectral analysis of laser Doppler radiation, only the absolute values $|f_{1\,max}|$ and $|f_{2\,max}|$ are measured. Therefore, $\Delta f$ in Eq. 2 is equal to $|f_{2\,max}|-|f_{1\,max}|$. It will be recognized that an erroneous value of $V_{max}$ results if $f_{1\,max}$ and $f_{2\,max}$ are of a different sign.

Figure 6:
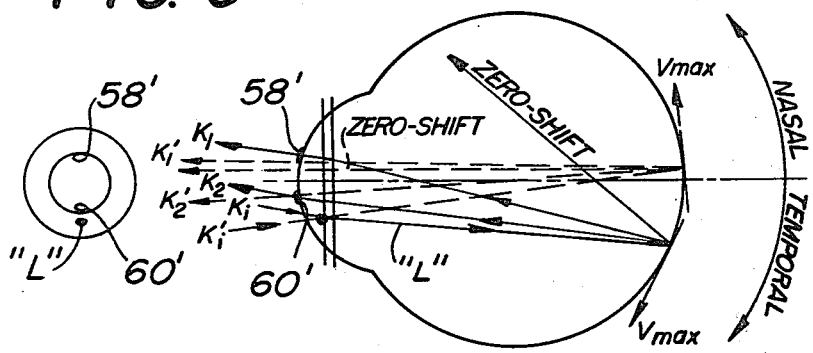
FIG. 6 is a schematic eye illustrative of a preferred orientation of the laser beam and the site of measurement in using the present apparatus.

Referring now to FIG. 6, it will be recognized that if $\overline{K_1}$, $\overline{K_2}$ and $\overline{V}_{max}$ lie in the same plane, $f_{1\,max}$ and $f_{2\,max}$ will be of the same sign if both $\overline{K_1}$ and $\overline{K_2}$ are in the same region of the plane when this plane is divided into two domains separated by the vector in the direction of zero Doppler shift, i.e., the vector with components $(-K_{ix}, K_{iy}, 0)$ (see C. E. Riva, G. T. Feke, B. Eberli and B. Benary, supra). When $\overline{K_1}$ and $\overline{K_2}$ are in separate regions of the plane $f_{1max}$ and $f_{2\,max}$ will be of different sign. With the present apparatus 10, error caused by different sign of $f_{1\,max}$ and $f_{2\,max}$ is avoided if the incident laser beam L is aligned so that it enters the eye at a point approximately along the line connecting the virtual apertures 58' and 60' and on the same side of the eye as the site of measurement, i.e., temporal to 58' and 60' when 58' and 60' are in the horizontal plane and the site of measurement is in the temporal fundus.

FIG. 6 illustrates the above relationships, and explains how the position and direction of the incident laser beam L at the cornea can insure that $f_{1\,max}$ and $f_{2\,max}$ are of the same sign. With reference to FIG. 6, both cutoff frequencies ($f_{1\,max}$ and $f_{2\,max}$) will be of the same sign if the incident beam, denoted in FIG. 6 by vector $K_i$, enters the eye on the same side of the eye as the site of the measurement. The solid lines in FIG. 6 illustrate this situation. In the scattering geometry drawn in dotted lines, the incident laser beam enters on the temporal side of the eye but the site of measurement is on the nasal side. The direction of zero Doppler shift lies between the scattered rays $\overline{K_1}'$ and $\overline{K_2}'$, and in this case, $f_{1\,max}$ and $f_{2\,max}$ are of a different sign.

Figure 7:
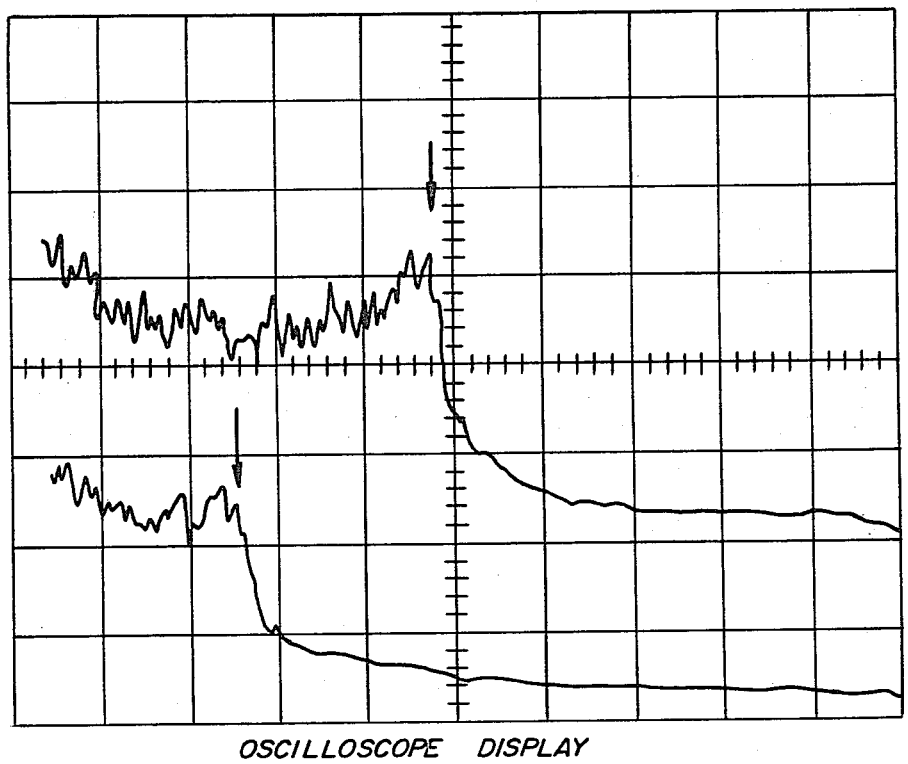
FIG. 7 is an illustration of two Doppler shift frequency spectra (DSFS) recorded simultaneously for two directions of scattered light from a suspension of polystyrene spheres in water.

FIG. 7 illustrates the results of in vitro measurements using the velocimeter 10, and shows DSFS recorded simultaneously for two directions of the scattered light from a suspension of 0.3 $\mu$m polysterene spheres in water flowing through a 200 $\mu$m internal diameter glass capillary tube. The tube was mounted vertically in the retinal plane of a Topcon model eye. The apertures (58, 60) made an angle of $30° \pm 1°$ with the tube. DSFS obtained from polysterene spheres in water flowing through capillary tubes are essentially flat up to a cutoff frequency $f_{max}$ and then abruptly fall to the baseline. $f_{max}$ corresponds to the maximum speed, $V_{max}$, at the center of the tube (see C. E. Riva, B. Ross and G. B. Benedek, supra).

The difference between the cutoff frequencies, read from the cursor of the spectrum analyzer (Unigon Industries, Inc., Model 4520, two-channel digital signal analyzer) was $1140 \pm 100$ Hz. $V_{max}$ was calculated from the relation $V_{max} = \lambda \Delta f / \Delta\alpha \cos 30°$ which takes into consideration the refraction of the scattered beams at the surface of the tube. $\Delta\alpha = 0.242\, d/f_r$, where $f_r$ is the focal length of the Topcon model eye ($48 \pm 2$ mm) and d, the distance between 58 and 60 ($8.7 \pm 0.1$ mm). With these values, $V_{max} = 1.90$ cm/sec. $V_{max}$ determined from the relation $F = SV_{max}/2$, where F is the pump flow rate, and S, the cross section of the tube, was 2.02 cm/sec. The difference between these values of $V_{max}$ can be accounted for by an error in $\Delta\alpha$ and $\Delta f$.

Figure 8:
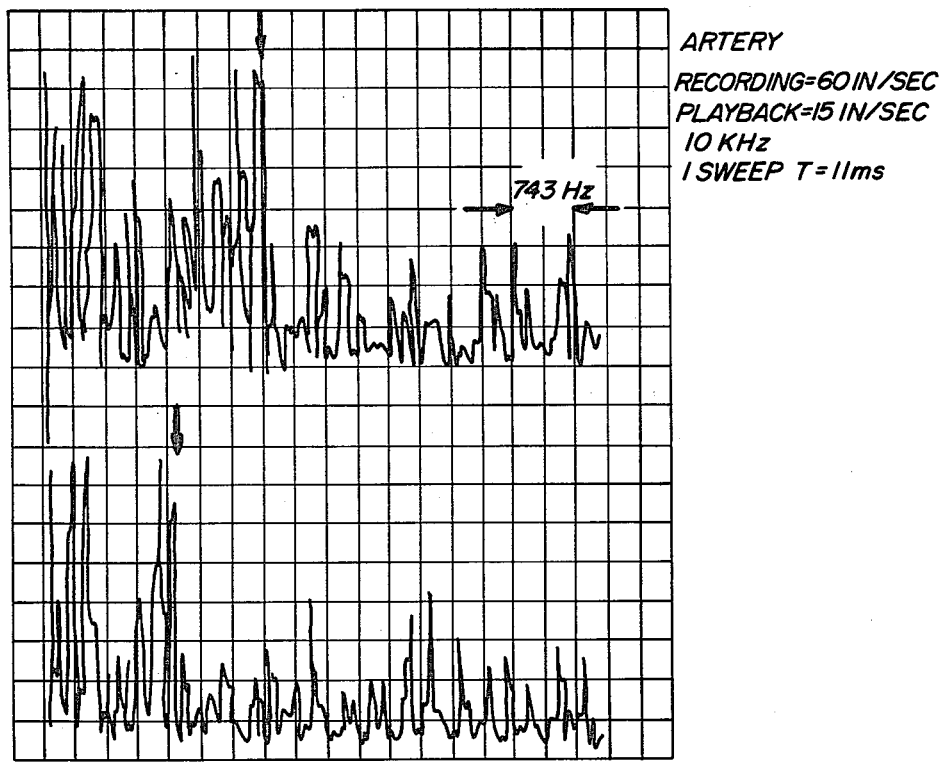
FIG. 8 is an illustration of two Doppler shift frequency spectra (DSFS) recorded simultaneously for two directions of scattered light from a main retinal artery of a subject eye.

FIG. 8 illustrates the results of in vivo measurements using the velocimeter 10. Two DSFS recorded simultaneously in 11 milliseconds from a main retinal artery of a normal volunteer during diastole are seen in FIG. 8. It will be noted that DSFS recorded in short measurement times from blood flowing in retinal vessels exhibit large fluctuations of spectral power up to a frequency $f_{max}$ which corresponds to $V_{max}$. These fluctuations arise from statistical fluctuations in the number of red blood cells giving rise to a particular Doppler frequency shift and from the statistical nature of the photocurrent. Both types of fluctuations and their dependence upon the measurement time have been investigated experimentally and theoretically (see, e.g. C. E. Riva and G. T. Feke, Application of Laser Doppler Velocimetry to Measurement of Retinal Blood Flow, *Current Laser Technology in Medicine and Surgery*, L. Goldman, Editor, Springer Verlag, New York (1981)).

The Doppler signals from the artery were recorded on a 4-channel FM tape recorder at a speed of 60 in/sec. For analysis, they were played back at a speed of 15 in/sec. Irradiance provided by the laser beam to the artery was approximately 0.05 w/cm². Angle $\beta$ was 23°. $f_{1\,max}$ and $f_{2\,max}$, determined by visual inspection of the spectra are respectively 10104 and 5944 Hz. Using Eq. 6, with $e=24.4$ mm, $d=8.5$ mm and assuming n to be equal to the index of refraction of the vitreous (1.336), $V_{max}$ was found to be 2.39 cm/sec, a value in the range of those obtained from retinal arteries of experimental animals (C. E. Riva, G. T. Feke, B. Eberli and V. Benary, supra; C. J. Bulpitt, E. M. Kohner and C. T. Dollery, *Bibl. Anat.* 11,448 (1973)).

Referring now to FIGS. 9 and 10, the manner in which the rhomboid prism 40 and rotary prism 46 serve to adjust the position and angle of entrance of the laser beam L will now be described in somewhat greater detail. With reference to FIG. 9, the beam L, it will be seen, impinges on the rhomboid prims 40, and has already been explained, is deflected by the beamsplitter 42, attenuated by the filter 44 and then passed through the rotary prism 46. FIG. 9, taken in conjunction with FIG. 10, shows how 360° rotation of the rhomboid prims 40 provides for rough adjustment of the position of the beam L. With reference to FIG. 10, rotation of the rhomboid prism 40 places the point of entry of the beam L at any selected point "P" on a circle lying within the annulus of illumination (at the eye pupil) provided by the above-described fundus illumination system. Fine adjustment of the position "P" within the annulus may be had by adjusting the dioptric power of the rotary prism 46 and by rotating the rotary prism 46. Referring again to FIG. 9, rotation of the rotary prism 46 alters the position and angle of incidence of the beam L as shown by means of dotted lines L' and L".

The present invention may be embodied in other specific forms without departing from its spirit or essential attributes, and, accordingly, reference should be made to the appended claims rather than the foregoing specification and accompanying drawings as indicating the scope of the invention.

I claim:

1. Apparatus for absolute measurement of blood flow in retinal vessels, comprising a laser for producing a beam of radiation, means for impinging the beam on at least one retinal vessel in which blood is flowing, means for producing from radiation of the beam scattered by the vessel and the red blood cells flowing therein a bidirectional pair of beams, said last-mentioned means comprising a pair of apertures disposed in the path of the radiation scattered by the vessel and the red blood cells flowing therein, means for detecting and collecting the pairs of beams to provide simultaneous signals representative of the Doppler shift frequencies of the radiation comprising the reflected beams, and means for producing from the signals an output representative of the absolute velocity of the red blood cells.

2. Apparatus in accordance with claim 1, and a plurality of pairs of apertures, said pairs being coplanar but having differing angular orientations in a plane generally perpendicular to the beams, and means for selectively placing one of said pairs of apertures in the optical path of the radiation reflected from the vessel.

3. Apparatus in accordance with claim 2, and means operatively associated with at least one of said apertures to separate the reflected beams.

4. Apparatus in accordance with claim 3, wherein said means operatively associated with at least one of said apertures comprises prism means.

5. Apparatus for measurement of retinal blood flow comprising a light source for illumination of the fundus of the eye, means for directing light from said source to the fundus to illuminate the fundus, a laser for producing a beam of radiation, radiation directing means whereby said beam may be directed to the fundus in association with the light, aiming means associated with said radiation directing means whereby the beam may be aimed at a blood vessel in the fundus, and means for detecting and collecting radiation scattered by the vessel and the red blood cells therein in two directions separated by a known angle, said last-mentioned means comprising at least one pair of apertures disposed in the path of radiation scattered by the vessel and the red blood cells therein so that radiation passing through said apertures is made to define two beams of scattered radiation.

6. Apparatus in accordance with claim 5, and means operatively associated with at least one of said apertures to separate the reflected beams.

7. Apparatus in accordance with claim 6, wherein said means operatively associated with at least one of said apertures comprises prism means.

8. Apparatus in accordance with claim 5, and a plurality of pairs of apertures, said pairs being coplanar but having differing angular orientations in a plane generally normal to the beams, and means for selectively placing one of said pairs of apertures in the path of radiation reflected from the vessel.

9. Apparatus in accordance with claim 8, and means operatively associated with at least one aperture of each of said pairs to separate the reflected beams.

10. Apparatus in accordance with claim 9, wherein said means operatively associated with at least one aperture comprises a prism.

11. Apparatus in accordance with claim 5, and a rotatable member disposed in the path of radiation reflected from the vessel and generally perpendicular thereto, a plurality of pairs of apertures circumferentially spaced in said member, the respective pairs of apertures being so oriented that lines drawn between the centerlines of the apertures of the respective pairs intersect radii of said member at different angles.

12. Apparatus in accordance with claim 11, wherein lines drawn between the centerline of the apertures of the respective pairs intersect radii of said member at angles of about 90°, −30° and 30°, respectively.

13. Apparatus for measurement of retinal blood flow comprising a light source for illumination of the fundus of the eye, means for directing light from said source to the fundus to illuminate the fundus, a laser for producing a beam of radiation, radiation directing means whereby said beam may be directed to the fundus in association with the light, aiming means associated with said radiation directing means whereby the beam may be aimed at a blood vessel in the fundus, and means for detecting and collecting radiation scattered by the vessel and the red blood cells therein in two directions separated by a known angle, said light source providing an annular field of illumination, said aiming means comprising first movable prism means for selectively positioning the beam of radiation within the annular field, and second prism means having variable dioptric power for fine adjustment of the position and of the angle of entrance of the beam.

14. Apparatus in accordance with claim 13, wherein said first prism means is a rhomboid prism.

15. Apparatus in accordance with claim 14, wherein said first prism means is a rhomboid prism and said second prism means is a rotary prism with variable dioptric power.

* * * * *